United States Patent
Wen (10) Patent No.: US 10,426,159 B1
(45) Date of Patent: Oct. 1, 2019

(54) HIGHLY EFFICIENT ENHANCERS FOR ANTIFREEZE PROTEIN ACTIVITY

(71) Applicant: The Trustees of California State University, Los Angeles, CA (US)

(72) Inventor: Xin Wen, Alhambra, CA (US)

(73) Assignee: The Trustees of California State University, Los Angeles, CA (US)

( * ) Notice: Subject to any disclaimer, the term of this patent is extended or adjusted under 35 U.S.C. 154(b) by 1276 days.

(21) Appl. No.: 13/835,734

(22) Filed: Mar. 15, 2013

Related U.S. Application Data (60) Provisional application No. 61/651,484, filed on May 24, 2012.

(51) Int. Cl.
| | | |
|---|---|---|
| *A61K 47/42* | (2017.01) | |
| *A01N 1/02* | (2006.01) | |
| *A01N 3/00* | (2006.01) | |
| *A23L 3/3472* | (2006.01) | |

(52) U.S. Cl.
CPC ............ *A01N 1/0221* (2013.01); *A01N 3/00* (2013.01); *A23L 3/3472* (2013.01)

(58) Field of Classification Search
CPC ........ G01S 19/235; G01S 19/25; G01S 19/26; A61K 47/42; A61K 38/28; A61K 47/26; A61K 9/19; C07K 14/43563; C13K 13/00; A01N 1/0221; C07H 19/06; C07H 19/16; C07H 1/06; C12N 1/04; C12N 9/96; G01N 33/483
See application file for complete search history.

(56) References Cited

U.S. PATENT DOCUMENTS

| | | |
|---|---|---|
| 6,793,952 B2 | 9/2004 | Fenn et al. |
| 6,914,043 B1 | 7/2005 | Chapman et al. |
| 7,968,767 B2 | 6/2011 | Demmer et al. |
| 2005/0161631 A1 | 7/2005 | Walker et al. |
| 2010/0068692 A1 | 3/2010 | Ben et al. |
| 2010/0312045 A1* | 12/2010 | Ramlov ............ A01N 1/02 600/35 |

OTHER PUBLICATIONS

Olijve et al. (2016) PNAS 113(14): 3740-45.*
Gomi et al. (2002) Gene 294: 157-66.*
Wen et al. (2011) J. Mol. Recog. 24(6): 1025-32.*
Wang et al. (2009) Biochemistry 48(40): 9696-9703.*
Wen et al. (2011) Journal of Molecular Recognition 24(6): 1025-1032 (Year: 2011).*
Amornwittawat, N. et al., "Polycarboxylates enhance beetle antifreeze protein activity," Biochimica et Biophysica Acta 1784 (2008):1942-1948.
Amornwittawat, N. et al., "Effects of polyhydroxy compounds on beetle antifreeze protein activity," Biochimica et Biophysica Acta 1794 (2009): 341-346.
Wang, S. et al., "Arginine, a Key Residue for the Enhancing Ability of an Antifreeze Protein of the Beetle Dendroides canadensis," Biochemistry 48 (2009): 9696-9703.
Wang, S. et al., "Hofmeister Effects of Common Monovalent Salts on the Beetle Antifreeze Protein Activity," J Phys Chem Letters 113 (2009): 13891-13894.
Wen, X. et al., "Interaction of reduced nicotinamide adenine dinucleotide with an antifreeze protein from Dendroides canadensis: mechanistic implication of antifreeze activity enhancement," J. Mel. Recognit. 24 (2011): 1024-1031.

* cited by examiner

Primary Examiner — Lisa J Hobbs
(74) Attorney, Agent, or Firm — Andrew D. Fortney; Central California IP Group, P.C.

(57) ABSTRACT

New, highly efficient enhancers for AFPs have now been discovered in the form of co-enzymes, and active fragments and mimetics thereof. These enhancer molecules do not have TH activity themselves, but can enhance the TH activity of AFPs by at least about 2-11 times. These molecules are so far the most effective enhancers for AFPs, and are characterized by containing coenzymes or fragments or mimetic thereof.

24 Claims, 8 Drawing Sheets

Specification includes a Sequence Listing.

SEQUENCE LISTING

<160> NUMBER OF SEQ ID NOS: 2

<210> SEQ ID NO 1
<211> LENGTH: 108
<212> TYPE: PRT
<213> ORGANISM: Dendroides canadensis

<400> SEQUENCE: 1

```
Met Val Trp Val Cys Lys Ser Ser Ile Leu Val Ile Ser Val Val Leu
1               5                   10                  15

Met Tyr Val Cys His Glu Cys Tyr Gly Gln Cys Thr Gly Gly Ser Asp
            20                  25                  30

Cys Arg Ser Cys Thr Val Ser Cys Thr Asp Cys Gln Asn Cys Pro Asn
        35                  40                  45

Ala Arg Thr Ala Cys Thr Arg Ser Ser Asn Cys Ile Asn Ala Leu Thr
    50                  55                  60

Cys Thr Asp Ser Tyr Asp Cys His Asn Ala Glu Thr Cys Thr Arg Ser
65                  70                  75                  80

Thr Asn Cys Tyr Lys Ala Lys Thr Cys Thr Gly Ser Thr Asn Cys Tyr
                85                  90                  95

Glu Ala Thr Ala Cys Thr Asp Ser Thr Gly Cys Pro
            100                 105
```

<210> SEQ ID NO 2
<211> LENGTH: 83
<212> TYPE: PRT
<213> ORGANISM: Dendroides canadensis

<400> SEQUENCE: 2

```
Gln Cys Thr Gly Gly Ser Asp Cys Arg Ser Cys Thr Val Ser Cys Thr
1               5                   10                  15

Asp Cys Gln Asn Cys Pro Asn Ala Arg Thr Ala Cys Thr Arg Ser Ser
            20                  25                  30

Asn Cys Ile Asn Ala Leu Thr Cys Thr Asp Ser Tyr Asp Cys His Asn
            35                  40                  45

Ala Glu Thr Cys Thr Arg Ser Thr Asn Cys Tyr Lys Ala Lys Thr Cys
    50                  55                  60
```

```
Thr Gly Ser Thr Asn Cys Tyr Glu Ala Thr Ala Cys Thr Asp Ser Thr
65                  70                  75                  80
Gly Cys Pro
```

HIGHLY EFFICIENT ENHANCERS FOR ANTIFREEZE PROTEIN ACTIVITY

FEDERAL FUNDING STATEMENT

This work was supported by Grant NIH GM088249.

SEQUENCE LISTING

The present application incorporates by reference a Sequence Listing in the ASCII text file identified by the file name "CSULA-004 SEQ LISTING 20180124_ST25.txt", created on Jan. 24, 2018, and having a size of 2,063 bytes.

FIELD OF THE INVENTION

The present invention relates generally to the use of common coenzymes, and active fragments and mimetics thereof, for enhancing the effects of antifreeze proteins.

BACKGROUND

Antifreeze proteins (AFPs) have been identified in many organisms (e.g., fish, plants, and insects) to allow these organisms to survive at sub-freezing temperatures. AFPs adopt diverse structures, but they all noncolligatively depress the freezing point without altering the melting point.

By definition, the equilibrium melting point and freezing points of water are identical. However, thermal hysteresis (TH) proteins, identified in some species of fish, insects, plants, fungi and bacteria have the ability to lower the non-equilibrium freezing point of water without lowering the melting point (equilibrium freezing point). Thus, when TH proteins are added to a solution, they produce a difference between the freezing point and melting temperatures of the solution.

In the absence of a TH protein, a small ice crystal of approximately 0.25 mm in diameter that is about to melt at the melting point temperature will normally grow noticeably if the temperature is lowered by 0.01° to 0.02° C. However, in the presence of a TH protein, the temperature may be lowered by about 1° to 6° C. below the melting point before noticeable ice crystals form, depending upon the specific activity of the protein, the size of the initial ice crystal, the rate of temperature reduction, and the concentration of the protein present. Because of their ability to lower the freezing point of aqueous solutions, these TH proteins are commonly referred to as antifreeze proteins (AFPs). However, unlike antifreezes such as glycerol, antifreeze proteins lower the freezing point of aqueous solutions via a non-colligative mechanism that does not depress the vapor pressure or raise the osmotic pressure of water. Antifreeze proteins also inhibit the recrystallization of ice, a phenomenon wherein grains of small polycrystalline ice change size and shape when held for a prolonged period of time at a sub-melting temperature.

It is generally-accepted that AFPs function through an adsorption-inhibition process. AFPs adsorb onto ice crystal surfaces and produce curved growth fronts of ice. Because of the unfavorable free energy of the curved fronts, the growth of the ice is inhibited. Insect AFPs are usually much more active than fish and plant AFPs. AFPs in fish blood typically produce TH activities of ~0.7-1.5° C. at ~20-30 mg/mL and relatively weaker AFPs in plants have TH activities of ~0.2-0.5° C. AFPs in insect hemolymph (at much lower concentrations compared to those in fish AFPs) are more active, usually having TH activities of ~3-6° C.

Antifreeze activity of some AFPs can be further enhanced by certain solutes (e.g., sodium chloride, potassium chloride, and glycerol). In the fire-colored beetle *Dendroides canadensis*, known enhancers of AFPs include some proteins (e.g., antibodies and other AFP isoforms) and common small molecules (e.g., polycarboxylates and polyols). For example, in the *Dendroides canadensis* hemolymph, glycerol and trehalose have been identified to enhance the antifreeze activity of AFPs from *D. canadensis* (DAFPs). The purified DAFPs produce less TH activity than the hemolymph itself. These solutes, called enhancers for AFP activity, do not have antifreeze activity themselves.

Noncolligative and natural properties make AFPs superior antifreeze agents over traditional antifreezes, such as glycerol and propylene glycol. At similar concentrations, AFPs are at least 100 times more powerful than common antifreeze agents.

AFPs have been suggested for enhancement of the cryopreservation of biological samples, for inhibition of formation and reformation of clathrate hydrate, for increasing the freezing tolerance of specific fish and plants, and for improvement of the quality of frozen foods. Identification of highly efficient enhancers for antifreeze protein activity can facilitate the commercial application of AFPs. In the presence of enhancers, the antifreeze activity of the AFP solution is enhanced and the amount of AFPs in the solution can be decreased.

SUMMARY OF THE INVENTION

AFPs have been found in many organisms creating a difference between the noncolligative freezing point and the melting point. This noncolligative property makes them very powerful freezing point depressants and having important applications in many areas, such as cold storage and preservation for cells, tissues and organs, in agriculture, and in the food industry. To further increase the antifreeze activity (or TH activity) of AFPs and decrease the required amount of AFPs is one of the major concerns in the applications of AFPs.

New, highly efficient enhancers for AFPs have now been discovered in the form of co-enzymes, and active fragments and mimetics thereof. These enhancer molecules do not have TH activity themselves, but can enhance the TH activity of AFPs by at least 2-11 times. These molecules are so far the most effective enhancers for AFPs, and are characterized by containing coenzymes or fragments or mimetics thereof.

DETAILED DESCRIPTION

Throughout this specification, the terms "a" and "an" and variations thereof represent the phrase "at least one." In all cases, the terms "comprising", "comprises" and any variations thereof should not be interpreted as being limitative to the elements listed thereafter. Unless otherwise specified in the description, all words used herein carry their common meaning as understood by a person having ordinary skill in the art. In cases where examples are listed, it is to be understood that combinations of any of the alternative examples are also envisioned. The scope of the invention is not to be limited to the particular embodiments disclosed herein, which serve merely as examples representative of the limitations recited in the issued claims resulting from this application, and the equivalents of those limitations.

Throughout this specification, the following abbreviations apply: AFP, antifreeze protein; TH, thermal hysteresis; DSC, differential scanning calorimetry; DAFP, *Dendroides*

*canadensis* antifreeze protein; MALDI-TOF, matrix-assisted laser desorption/ionization time-of-flight; HPLC, high-performance liquid chromatography; NADPH, (3-nicotinamide adenine dinucleotide phosphate, reduced; NADP, (3-nicotinamide adenine dinucleotide phosphate; NADH, (3-nicotinamide adenine dinucleotide, reduced; TTHA, triethylenetetramine-N,N,N',N'',N''',N'''-hexaacetate; NAD, (3-nicotinamide adenine dinucleotide; TNAD, thionicotinamide adenine dinucleotide; PAAD, 3-pyridine aldehyde adenine dinucleotide; FAD, flavin adenine dinucleotide; CoA, coenzyme A; RSP, D-ribose-5-pho sphate; ribose, D-(−)-ribose; AMP, (−)-adenosine 5'-monophosphate; ADP, adenosine 5'-diphosphate; ADPR, adenosine 5'-diphosphoribose. For simplicity, the positive charge is omitted from NAD, PAAD, and TNAD.

For purposes of the present invention, by "active fragments . . . thereof," when used with respect to enhancers, it is meant that the fragment exhibits comparable enhancer activity as compared to the full length co-enzyme from which the fragment was derived at an equivalent concentration. By "mimetic," it is meant to be inclusive of small organic molecules which exhibit similar enhancer activity as compared to the full length co-enzyme as described herein. Mimetics may be designed to have a similar structural shape(s) and/or functional group(s).

In proteins, arginine often serves as the positively charged center for the recognition and binding of anionic substrates, such as carboxylate and phosphate anions. It has been discovered that the enhancement effects of a series of coenzymes (e.g., NADP(H), NAD(H), FAD, and CoA) on the antifreeze activity of AFPs are greater than the previously identified most efficient naturally occurring enhancer TTHA. NADPH is demonstrated as the most efficient enhancer for antifreeze activity of arginine containing AFPs identified thus far. Furthermore, active molecular fragments of NADPH on the antifreeze activity of AFPs have also been discovered. Compositions within the scope of the present invention comprise an AFP, preferably an AFP containing arginine residue(s). Insect AFPs are preferable as their antifreeze activity is higher than those found in fish and plants.

Figure 1:
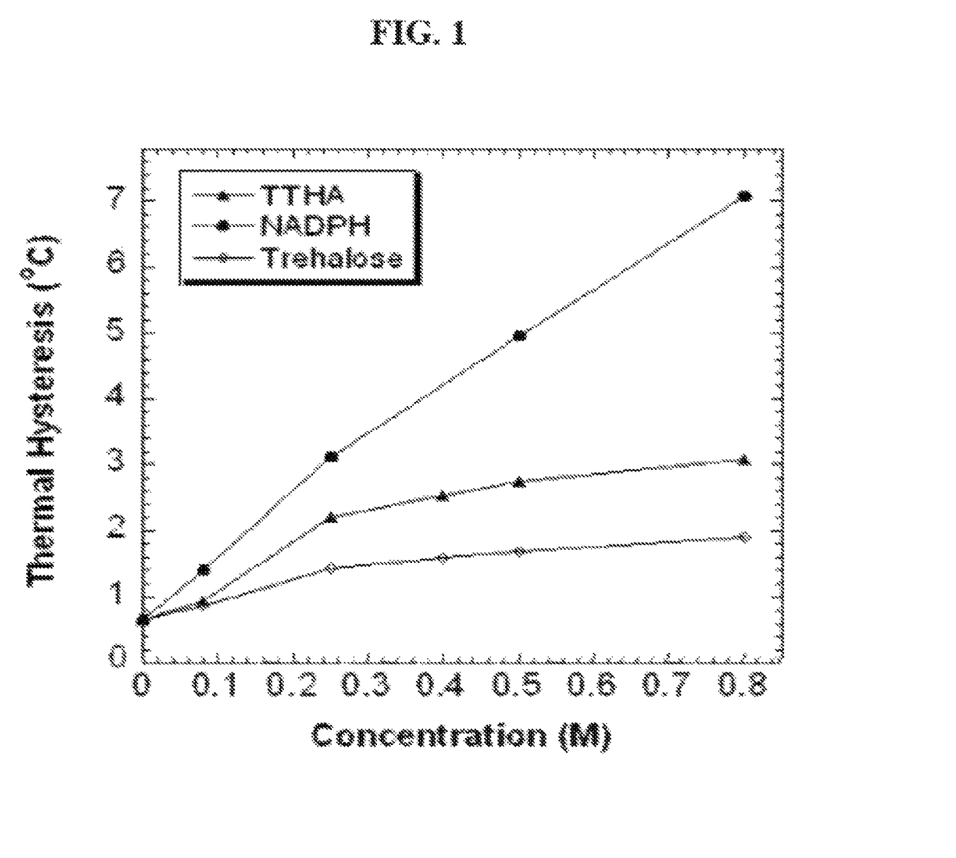

The TH activity of DAFP-1 can be enhanced by at least about 2-11 times in the presence of NADPH (FIG. 1). The enhancement ability of NADPH is much higher than any of the known enhancers of DAFP-1 activity, namely polycarboxylates such as TTHA and polyhydroxyls such as trehalose. The previously identified best carboxylate containing enhancer, TTHA, and hydroxyl containing enhancer, trehalose, are shown in FIG. 1 for comparison.

Figure 2:
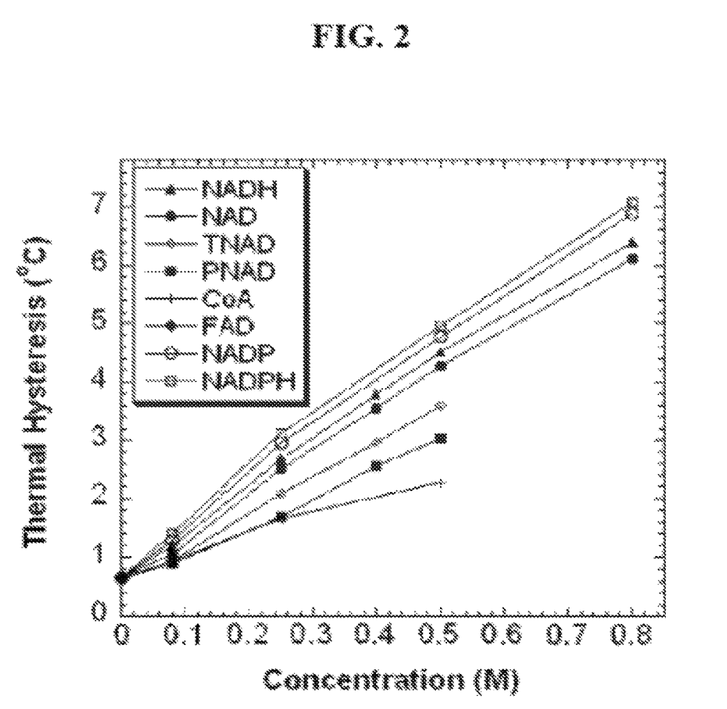
Figure 8A:
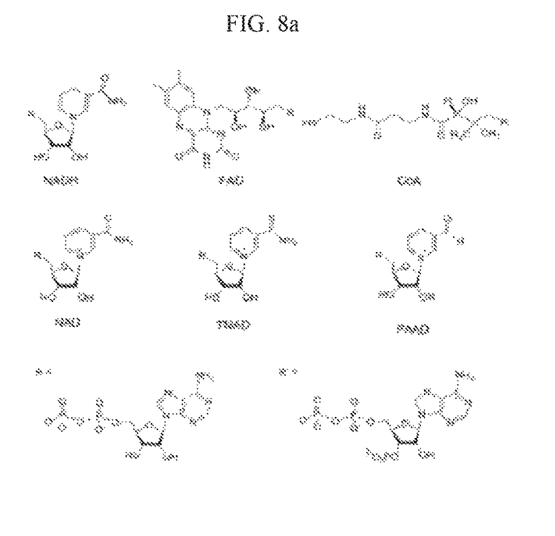
Figure 8B:
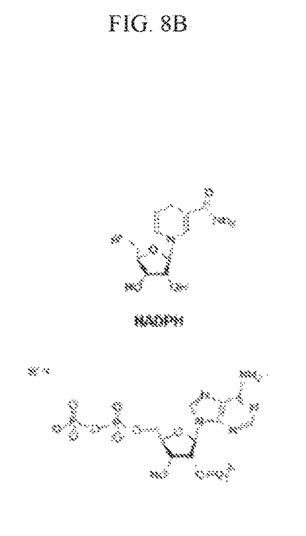

To examine the effects of changes in the structure of NADH on the TH activity of DAFP-1, a series of NADH analogs and other coenzymes were assessed for their enhancement abilities (FIGS. 8A-8B). The molar enhancement effectiveness order, NADH>NAD>TNAD>PAAD, was observed for the NADH analogs (FIG. 2).

The enhancement ability of NAD is very similar to that of its reduced form, NADH, although slightly lower. TNAD, in which the oxygen of the carboxamide is substituted by sulfur, and PAAD, in which the carboxamide is substituted by aldehyde, also show a very efficient enhancement ability of the TH activity of DAFP-1. The three analogs, NAD, TNAD, and PAAD, are more efficient than any previously identified enhancers for DAFP-1. Two other coenzymes, FAD and CoA, can enhance the TH activity of DAFP-1; however, their enhancement efficiencies are less than those of NADH and NAD analogs (FIG. 2). The data acquired for FAD is limited by its solubility in the test system.

Figure 3:
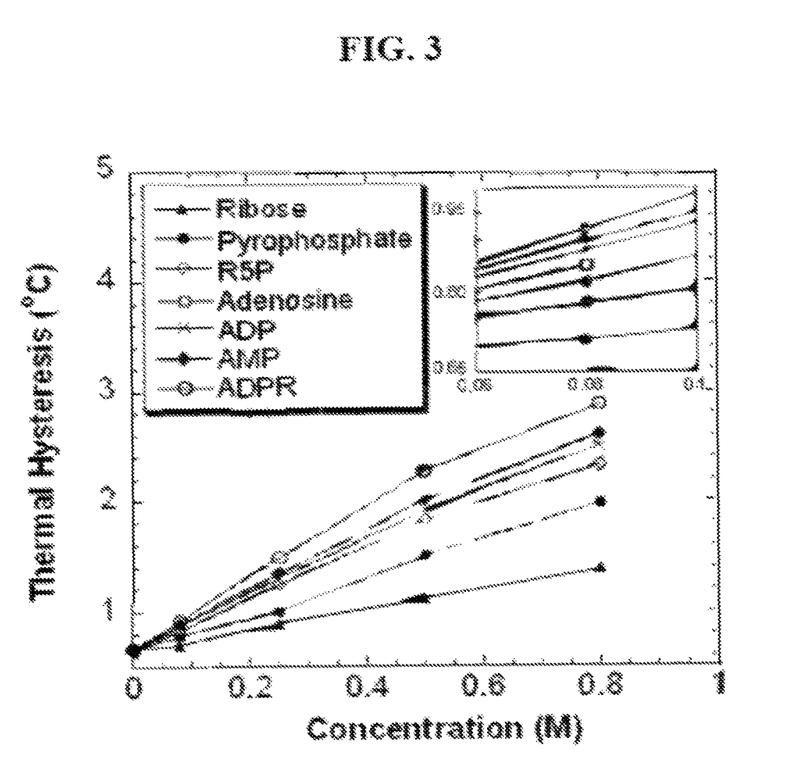
Figure 9:
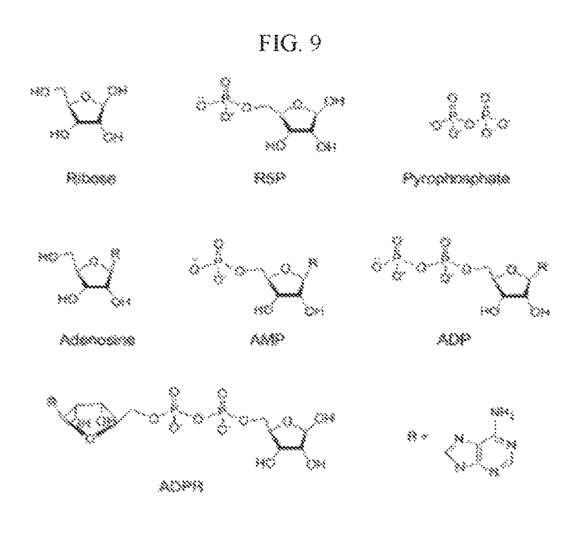

To examine the effects of structural moieties of NADH on the TH activity of DAFP-1, the enhancement effects of various molecular fragments of NADH were assessed (FIG. 9, see also FIG. 3). All the molecular fragments of NADH are less efficient enhancers for DAFP-1 compared to the entire molecule of NADH (FIG. 3). The following molar enhancement effectiveness order was observed for the selected fragments: ADPR>AMP>adenosine>R5P> pyrophosphate>ribose.

ADPR, which only lacks the nicotinamide, is the fragment containing the most structural moieties of NADH (FIG. 9). ADPR has the most efficient enhancement ability among these fragments (FIGS. 1 and 3). ADP lacks a ribose moiety compared to ADPR, and the TH enhancement ability of ADP is less than that of ADPR (FIG. 3). Adenosine lacks a phosphate group compared to AMP. At 0.080M, the enhancement ability of adenosine is lower than that of ADP. Data at higher concentrations, however, are not available for adenosine due to its low solubility. Ribose is the smallest structural component of NADH among the fragments; it also has the least enhancement of the TH activity of DAFP-1. This trend was also observed for the other fragments. Generally, the fragment containing more structural moieties of NADH appeared to have better enhancement efficiency for the TH activity of DAFP-1. The notable exception to this trend is the transposition of AMP and ADP in this series. The sum of the TH enhancements of the fragments that collectively constitute a complete NADH moiety is not equal to that of NADH alone. This indicates that the entire molecular structure of NADH is important for its extremely efficient enhancement of the TH activity of DAFP-1.

Figure 4:
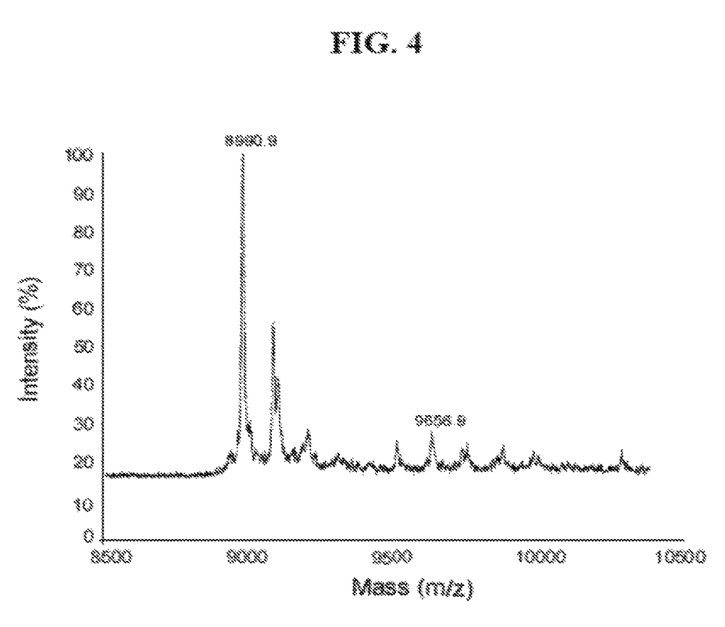

A 1:1 binding of NADH to DAFP-1 can be detected by MALDI-TOF mass spectrometry, indicating that the intact complex exists under the experimental conditions. The calculated molecular mass of DAFP-1 is 8968.8 Da. In FIG. 4, the Na+ adduct ion of DAFP-1 was observed as a major peak at m/z=8990.9. The peak observed at m/z=9656.9 corresponds to the Na+ adduct ion of the 1:1 complex of DAFP-1 and NADH.

The formation of 1:1 complex of DAFP-1 and NADH was further confirmed by HPLC analysis. With the gel filtration method of Hummel and Dreyer, the size exclusion column can be equilibrated with a buffer containing the ligand at a known concentration. The protein sample prepared in the buffer (containing the ligand at the same concentration) is injected into the equilibrated column. If binding occurs, the concentrations of the ligand in the elution buffer and in the elution are usually different. As a result, a positive peak corresponding to the protein (the ligated protein and the free protein if there is any) appears at the retention time of the macromolecule, followed by a trough at the retention time of the ligand, indicating the decrease of the ligand concentration due to the binding. The size exclusion column would not be able to discriminate between the free protein and the ligated protein if the size difference between the protein and the protein-ligand complex is beyond the limit of the column. The trough area depends directly on the amount of the bound ligand that is depleted by binding to the protein. The bound ligand can be determined more precisely using the internal calibration method.

Figure 5:
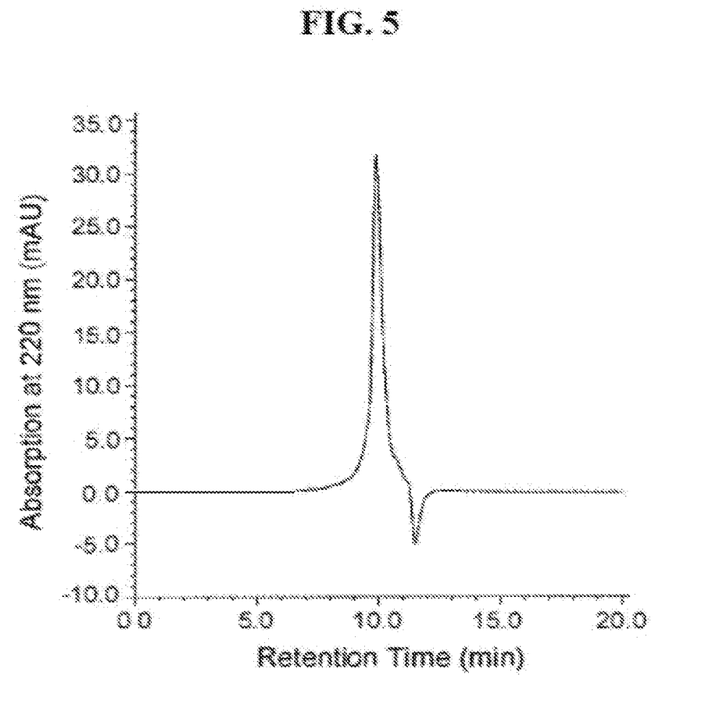
Figure 6:
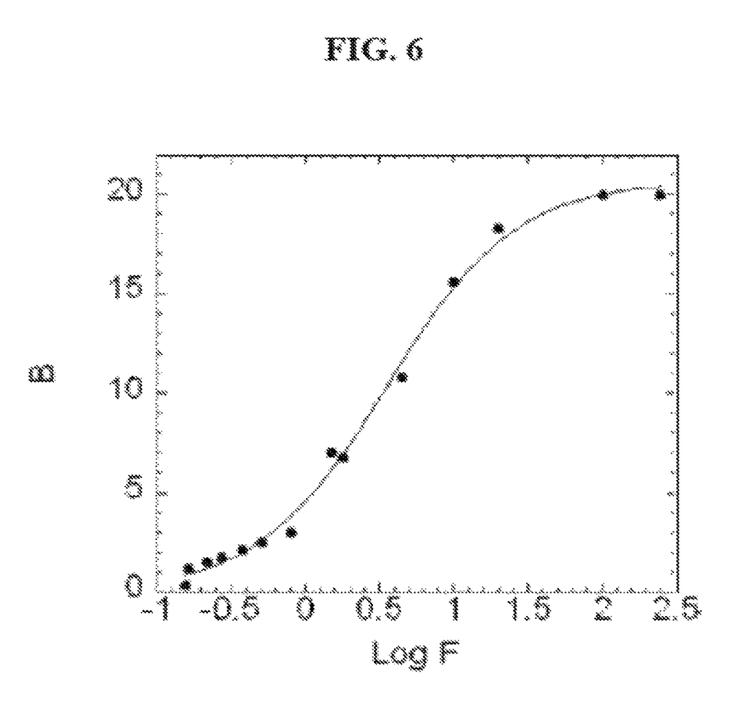

FIG. 5 shows a representative HPLC chromatogram of NADH binding to DAFP-1 using the Hummel and Dreyer method. DAFP-1 was eluted at 10.0 min. The amount of NADH in the column depleted by binding to DAFP-1 was observed as a trough at 11.5 min. The resulting semilog plot is shown in FIG. 6. The curve fitting results suggest that the binding of NADH to DAFP-1 is characterized by a $K_d$ of 0.28±0.02 µM and a stoichiometry of 1:1, however, non-specific binding of two or multiple NADH molecules to a single DAFP-1 may occur.

Examination of the enhancement abilities of the various NADH analogs and their structures suggest that the modifications of the nicotinamide ring generate a series of highly efficient enhancers whose enhancement abilities are stronger than that of any previously identified enhancers but weaker than that of NADH. NAD has the most similar structure, and its enhancement effect is comparable to that of NADH. Compared to NAD, the sulfur replaces oxygen in the carboxamide moiety of TNAD, and the carboxamide group is replaced by an aldehyde in PAAD. TNAD and PAAD are less efficient enhancers than NAD, and PAAD is the least effective enhancer among the analogs. The results suggest that the carboxamide moiety is important for the greatest enhancement.

The investigation of the enhancement of various molecular fragments of NADH indicated that all the active molecular fragments of NADH can enhance the TH activity but are much less effective than that of NADH. Thus, the whole molecular structure of NADH is important for its most efficient enhancement. Among the fragments, ADPR containing the most structural moieties of NADH (i.e., only lacks the nicotinamide) has the most efficient enhancement ability among the fragments; ribose, the smallest structural component of NADH, has the least enhancement effect. Generally, the fragment containing more structural moieties of NADH appears to have better enhancement efficiency for the TH activity. The relative enhancement efficiencies, AMP>ADP, however, cannot be explained by their molecular sizes. Compared to ADP, AMP lacks one phosphate group and is less negatively charged. The mechanism of the enhancer action has been suggested to involve the binding to an arginine in DAFP-1. Considering the free energy change of the ionic hydration, the binding of ADP to arginine is less favorable than the binding of AMP to arginine. The balance between ionic interaction and hydration in aqueous solution may be the explanation for our observation that the enhancement ability of ADP for the TH activity of DAFP-1 is lower than that of AMP.

The composition of efficient enhancers for AFPs including naturally occurring and synthetic compounds comprises:

(nitrogenous base-R1)$_l$-(carbohydrate moiety-R2 and/or R3)$_m$-(phosphate)$_n$-(carbohydrate moiety-R2 and/or R3)$_o$-(nitrogenous base-R4)$_p$ and salts and hydrates thereof,
where:
l=0 or 1;
m=0, 1, 2, 3, 4, 5, 6, 7, 8, 9, or 10;
n=0, 1, 2, 3, or 4;
o=0, 1, 2, 3, 4, 5, 6, 7, or 8; and
p=0 or 1;
with the proviso that only one of l, m, n, o, p may be 0; and where:
R1=H, COOH, CONH$_2$, COOCH$_3$, COOC$_2$H$_5$, COOC$_3$H$_7$, CONHCH$_3$, CON(CH$_3$)$_2$, CSNH$_2$, NH$_2$, NHCH$_3$, N(CH$_3$)$_2$, COH, F, Cl, Br, I, OH, OCH$_3$, or OC$_2$H$_5$;
R2=H or OPO$_3$H$_2$;
R3 is H or OPO$_3$H$_2$; and
R4 is H, COOH, CONH$_2$, COOCH$_3$, COOC$_2$H$_5$, COOC$_3$H$_7$, CONHCH$_3$, CON(CH$_3$)$_2$, CSNH$_2$, NH$_2$, NHCH$_3$, N(CH$_3$)$_2$, COH, F, Cl, Br, I, OH, OCH$_3$, or OC$_2$H$_5$.
R1 and R4 represent the substituents on the nitrogenous base. R2 and R3 represent the substituents on the carbohydrate moieties. The presence of heteroatom(s) in the carbohydrate does not affect the enhancement efficiency of the resulting compound.

Examples of enhancers are shown, but not limited to Formulas I-III:

Formula I where l=1, m=1, n=2, o=1, and p=1;

Formula II where l=0, m=2, n=0, o=2, and p=0, and R2, R3=H; and

Formula III where l+p_=3, and R1, R4=COOH.

The extent of TH enhancement by the exemplified enhancers for the MT's from *Dendroides canadensis* (DAFPs: DAFP-1, -2, -4, and -6 are provided. For purposes of example only, NADP and NADPH (l=1, m=1, n=2, o=1, p=1) can increase the TH activity of DAFPs by at least 15-fold; ATP (l=1, m=1, n=3) can increase the TH activity by at least 5-fold; 5-Fluorouridine (l=1, m=1, R1=F) and 2-fluoro-2-deoxy-D-glucose (m=1) can increase the activity by 2-fold.

We have hypothesized that extensive interactions, involving ionic binding, hydrogen bonding, and hydrophobic interaction, between an enhancer and DAFP-1 are required for the enhancer to be a highly efficient one. Ionic interactions are critical in the binding of the pyrophosphate moiety of NADH to the guanidinium group of arginine in DAFP-1. However, the ionic interaction between NADH and DAFP-1 alone cannot be very stable since the ion pair stability is greatly decreased by the hydration of the ions (i.e., the guanidinium in arginine and the phosphate in NADH) in aqueous solutions. To form a tight complex, the binding between DAFP-1 and NADH is likely to involve various interactions, including ionic interaction, hydrogen bonding, and hydrophobic interaction, with the involvement of other important amino acids in DAFP-1. For example, hydrophobic interactions may occur in the binding of the adenine moiety and the nicotinamide moiety of NADH to some nonpolar residues of DAFP-1, and hydrogen bonding may be essential for orientating the two ribose moieties of NADH in the binding.

Figure 7:
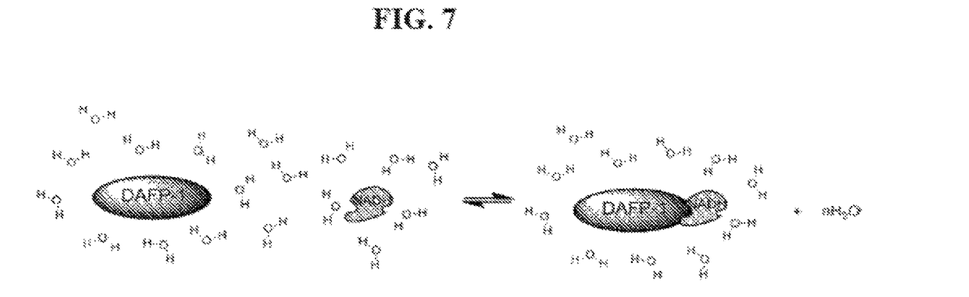

In aqueous solutions, DAFP-1 and enhancer molecules are solvated by water molecules. Therefore, effects on the surrounding water molecules must be taken into account. The water molecules bound to the interacting surfaces of DAFP-1 and NADH are expected to be released upon formation of the complex (FIG. 7). The released water into the bulk solution may result in a more disordered system (i.e., entropically favorable) counteracting the entropically unfavorable freezing process. Furthermore, guanidinium-phosphate interactions are generally enthalpically favorable. According to the adsorption-inhibition mechanism, by a simple estimation, the energy released upon the interactions may contribute to the inhibition of the growth of the ice fraction. The $K_d$ of the binding of NADH to DAFP-1 is in the micromolar range, which is in fast exchange regime on the NMR time scale in solution. The high concentration used for the enhancer may help shift the chemical equilibrium (FIG. 7) to the formation of the APP-enhancer complex, and the free enhancers in the solution rapidly exchange with the APP-bound enhancers, which allows NADH to continue to act as an enhancer as long as the enhancer and the APP molecules are stable in the solution. This dynamic process in solution may also provide a barrier for water to join the ice surface. Besides promoting the formation of APP-enhancer complexes, the high concentration of enhancer may salt out APP (i.e., the salting-out effect of the enhancers), which has been reported to contribute to the enhancement mechanism by small molecules. Thus, in contrast to the protein enhancers that help block a larger ice growth surface, different mechanisms seem to be involved in these low molecular mass enhancers.

NAD(H), FAD, and CoA, are prevalent coenzymes that play a central role in the metabolic activities of plants, animals, and microorganisms. DAFPs have been shown to be present in the hemolymph, gut fluid, and epidermis of *D. canadensis* larvae. The amounts of NADH in the those sites, however, are too limited to serve as an effective physiological enhancer for the TH activity of DAFPs despite its potent enhancement ability. In contrast, the previously identified polyol enhancers, such as glycerol and trehalose, may be present in all compartments of the insect and thus be available for enhancer function in vivo.

The subject invention is directed to methods and compositions relating to processes for preparing improved products, the improvements residing in enhanced antifreeze properties. The process comprises addition of at least one antifreeze polypeptide or protein, including recombinant forms. The antifreeze polypeptide or protein preferably comprises at least one arginine residue. Preferably, the antifreeze polypeptide or protein is derived from an insect. A preferred source of antifreeze polypeptide or protein is derived from *Dendroides canadensis*, or has an amino acid sequence substantially corresponding thereto. More preferably, the antifreeze polypeptide or protein is DAFP, including all isoforms, or has an amino acid sequence substantially corresponding thereto. Even more preferably, the antifreeze polypeptide or protein is DAFP-1, or has an amino acid sequence substantially corresponding to the one presented below from amino acid 28 through amino acid 108. The SEQ. ID 1 listed in this paragraph is identical to the sequence submitted in the text file named "DAFP1seq_ST25" and which is herein incorporated by reference. The text file, identified in the preceding sentence and incorporated by reference, was created on Apr. 14, 2015 and is 1.4 kB in size.

SEQ. ID 1: antifreeze protein-1E [*Dendroides canaclensis*] GenBank: AAB94307.1
MVWVC KSSIL VISVV LMYVC HECYG QCTGG SDCRS CTVSC TDCQN CPNAR
   5 10 15 20 25 30 35 40 45 50
TACTR SSNCI NALTC TDSYD CEINAE TCTRS TNCYK AKTCT GSTNC YEATA CTDST
   55 60 65 70 75 80 85 90 95 100 105
GCP
   108

The process further comprises addition of at least one AFP enhancer in the form of co-enzyme, active fragment and/or mimetic thereof. The enhancer preferably comprises at least one phosphate. The enhancer preferably is one or more of NADH, NAD, TNAD, and/or PAAD. The process further comprises addition of the AFP and the enhancer in an amount sufficient to affect ice crystal growth. The process further comprises an increase in TH of at least 2×, and more preferably of at least 4×, and even more preferably of at least 6×, and yet more preferably of at least 8× and most preferably of at least 10×.

The term "or has an amino acid sequence substantially corresponding thereto" comprises an amino acid sequence equal to the amino acid sequence of AFP isolated from *Dendroides canadensis*, in particular DAFP-1, and also comprises an amino acid sequence that differs by one or two amino acids from the known amino acid sequence but still encodes a polypeptide with the same AFP activity as the native protein. The mutations or differences may not be in amino acids known to be essential for activity of the polypeptide. Preferably any differences in amino acid sequence are silent mutations, whereby the substitutions are conservative substitutions that do not alter the hydropathy profile of the polypeptide and thus presumably do not severely influence the polypeptide structure and the activity, i.e., an amino acid with a hydrophobic side chain is preferably only exchanged for another amino acid with a hydrophobic side chain and an amino acid with a hydrophilic side chain is only replaced by another amino acid with a hydrophilic side chain. An amino acid sequence exhibiting homology above 60%, preferably more than 70%, and most preferably more than 80% can be expected to be representative of a polypeptide exhibiting similar properties to *Dendroides canadensis* AFP. In addition the polypeptide encoded by the amino acid sequence should exhibit at least the AFP activity of native DAFP. Recombinant AFP activity can be determined by carrying out comparisons with recrystalization assays using a series of dilutions of the polypeptide to be determined and equal amounts and dilutions of AFP as obtained from *Dendroides canadensis*. The manner in which such a recrystalization assay can be carried out and evaluated is known in the art.

The product can be a food product or a biological material. The biological material can for example be an animal organ or tissue, or it can be plant material. In particular recombinant polypeptide can be added. Preferably the polypeptide will be of food grade status in order to provide a final product with food grade status. Food products exhibit improved freezing qualities.

The products produced according to the invention exhibit improved properties due to modification of ice crystal growth processes influencing size and shape characteristics of ice, in particular in regrowth, thereby e.g. minimizing potential freezing damage, preventing or inhibiting ice recrystalization of the product upon freezing, and/or improving the overall characteristics of the products such as texture and stability. The process comprises addition of an enhancer and an AFP as described herein, or a host organism capable of expression of a recombinant polypeptide or protein with an amino acid sequence substantially corresponding to that of the AFP, to the non-improved product. For the purposes of this invention, the term "AFP" is considered to include recombinant forms. For food products, the AFP should be food-grade.

The enhancer and the AFP (including a host organism capable of secreting the AFP polypeptide or protein) may be added directly to the non-improved product or to an ingredient or mixture normally used to prepare the non-improved product. Alternatively, the secreted recombinant form of the AFP may be collected and then added to the non-improved product or to an ingredient or mixture normally used to prepare it. Steps normally undertaken to prepare the non-improved product also falls within the scope of the invention. The product can be a food product or a biological material. Examples of biological material include but are not limited to animal organ or tissue, and plant material.

EXAMPLES

Materials

The chemicals were ACS grade or better, and the high-performance liquid chromatography (HPLC)-grade solvents and chemicals were purchased from Sigma-Aldrich (St. Louis, Mo.). NADPH, NADP, NADH, NAD, thionicotinamide adenine dinucleotide (TNAD), 3-pyridine aldehyde adenine dinucleotide (PAAD), FAD, CoA, ribose, D-ribose-5-phosphate (R5P), pyrophosphate, adenosine, (−)-adenosine 5'-monophosphate (AMP), adenosine 5'-diphosphate (ADP), and adenosine 5'-diphosphoribose (ADPR) (Sigma) were used without additional purification. Milli-Q water produced from a Synergy water system (Millipore) with a minimum resistivity of 18MΩ·cm was used to prepare all the solutions.

DAFP-1 Sample Preparation

DAFP-1 was prepared as previously described (Amornwittawat et al., 2009). Briefly, DAFP-1 was expressed as a fusion protein containing a His tag in *Escherichia coli* Origami B cells. The cells were harvested by centrifugation at 4° C. and lysed by French press (Thermo Fisher). The crude protein was purified using Ni-NTA agarose (Qiagen). The tags were cleaved using enterokinase (New England Biolabs) and removed using Ni-NTA agarose. The cleaved protein was finally purified using ÄKTA Purifier 10 (GE Healthcare) with a Sephacryl S-100 gel filtration column (GE Healthcare). The identity of purified DAFP-1 was confirmed by SDS-PAGE, HPLC, and matrix-assisted laser desorption/ionization time-of-flight (MALDI-TOF) mass spectrometry. The protein concentration was determined by UV-Vis spectroscopy (Varian) using the absorption at 280 nm (Gill and von Hippel, 1989).

Antifreeze Activity Measurements

The antifreeze (or TH) activities of the samples were assessed using differential scanning calorimetry (DSC) following the known procedure (Amornwittawat et al., 2008). The measurements were performed on a DSC 823e (Mettler Toledo, Ohio) with an HSS7 high sensitivity sensor and a Julabo FT900 intracooler chiller (Julabo Company, Allentown, Pa.). The enhancement effects of the following compounds on the TH activity of DAFP-1 were assessed: NADH and the NADH analogs, including NAD, TNAD, PAAD, and two other coenzymes, FAD and CoA; the molecule fragments of NADH, including ribose, RSP, pyrophosphate, adenosine, AMP, ADP, and ADPR; and previously identified enhancers, triethylenetetramine-N,N,N',N",N"',N"'-hexaacetate (TTHA) and trehalose, for comparison. The concentrations of these potential enhancers were varied from 0.00M to 0.80M, depending on their solubilities. The concentration of DAFP-1 was 453 µM in all the samples, and the TH activity of the protein sample alone was 0.69±0.01° C. The TH activity of DAFP-1 is unchanged from pH 2 to pH 12. To eliminate possible enhancement effects of buffer compounds, the pHs of the samples were carefully adjusted using 0.30M HCl and 0.10M NaOH when necessary. The pH of the final samples was 7.5. Each combination of DAFP-1 and enhancer was prepared twice, and the TH of a given sample was measured at least twice. The TH values were presented as means, and the standard deviations were within 2% of the mean values.

MALDI Mass Spectometry

The experiments were performed on a PerSeptive Biosystems/Voyager-DE MALDI-TOF mass spectrometer at Stanford PAN facility. The mass spectrometer was calibrated using external mass standards before the sample analysis. A saturated solution of the matrix, sinapinic acid, was prepared in 1:1 (v/v) water:acetonitrile with 0.1% trifluoroacetic acid (TFA). The sample solution was made by mixing 2.0 µl of 150 µM DAFP-1 and 2.0 µl of 500 µM NADH (sodium salt), pH 7.5. The sample was then incubated for 30 min at 4° C. After desalting by Ziptip C18 resin (Millipore), the sample was dissolved in double-distilled $H_2O$ with 0.1% TFA, and 0.5 µl of the sample solution was mixed with an equal volume of the saturated matrix solution. The prepared sample mixture was then dropped in a MALDI sample plate and air dried before analysis.

Size-Exclusion HPLC Analysis of NADH Binding to DAFP-1

The binding of NADH to DAFP-1 was characterized using HPLC by an improved gel filtration method of Hummel and Dreyer (Hummel and Dreyer, 1962; Parsons, 1980). The Dionex HPLC system (Sunnyvale, Calif.) consisting of an Ultimate 3000 pump and an Ultimate 3000 Photodiode Array Detector was used in this study. A BioSuite 125, 4-µm UHR SEC HPLC column, 4.6×300 mm (Waters, Milford, Mass.) was equilibrated with buffer containing 0.10M Na2 SO4, 0.05% NaN3, 0.10M NaPi, and NADH at a desired concentration, pH 7.00. The DAFP-1 samples were prepared by adding a known amount of DAFP-1 in the above buffer. After equilibration for at least 30 min, the DAFP-1 sample was injected into the column. The injection volume was 10 µl in all experiments. Elution was performed at a flow rate of 0.5 ml/min at ambient temperature. The eluates were monitored at 220 nm. The experiments were performed at various concentrations of DAFP-1 (1.5-20 µM) and NADH (0-270 µM). The initial concentrations of NADH were determined using the molar extinction coefficient ($\epsilon 340=6.22\times 10^3 M^{-1} cm^{-1}$) (Dawson et al., 1985). The binding of NADH to DAFP-1 resulted in a trough at the retention time of NADH. The area of the trough depends directly on the amount of bound NADH that is depleted by binding to DAFP-1. The amount of bound NADH was determined by the internal calibration method (Parsons 1980; Sun and Hsiao, 1993). The amount of free NADH is obtained from the difference of total NADH and calculated bound NADH. The Klotz plot (or semilog plot) was used to analyze the binding data (Klotz, 1982). The dissociation constant ($K_d$) and stoichiometry for the binding of NADH to DAFP-1 were estimated by curve fitting using nonlinear regression analysis.

Results

The TH activity of DAFP-1 can be enhanced by at least about 2-11 times in the presence of NADH as illustrated in FIG. 1. A series of NADH analogs and other co-enzymes were assessed for their enhancement abilities as illustrated in FIGS. 8A-8B. The molar effectiveness enhancement order was observed for the NADH analogs as illustrated in FIG. 2. ADPR is the fragment containing the most structural moieties of NADH as illustrated in FIG. 9. ADPR has the most efficient enhancement ability among the fragments tested as illustrated in FIG. 3. A 1:1 binding of NADH to DAFP-1 is shown by MALDI-TOF mass spectrometry showing a Na+ adduct ion of DAFP-1 as a major peak at m/z=8990.9 and the Na+ adduct ion of the 1:1 complex of DAFP-1 and NADH as illustrated in FIG. 4. A representative HPLC chromatogram of NADH binding to DAFP-1 is illustrated in FIG. 5. Characterization of binding of NADH to DAFP-1 by a $K_d$ of 0.28±0.02 µM and a stoichiometry of 1:1 as illustrated in FIG. 6. Other observations and analysis is discussed throughout this specification.

The invention claimed is:

1. A process for increasing the thermal hysteresis of an antifreeze protein, comprising:
selecting (i) an antifreeze protein from the group consisting of polypeptides or proteins having at least the following partial amino acid sequence of DAFP-1 (SEQ ID NO: 2):

```
QCTGG SDCRS CTVSC TDCQN CPNAR TACTR
      SSNCI NALTC TDSYD CHNAE TCTRS
      TNCYK AKTCT GSTNC YEATA CTDST
      GCP,
``` and polypeptides or proteins having an amino acid sequence that differs from the above partial amino acid sequence of SEQ ID NO: 2, but that exhibits more than 60% homology with the above partial amino acid sequence of SEQ ID NO: 2 and contains at least one arginine residue, wherein said antifreeze protein has a baseline thermal hysteresis, and (ii) an enhancer selected from the group consisting of: NADH, NAD, TNAD, PAAD, CoA, FAD, NADP, NADPH, fragments and analogs thereof having a formula:

(nitrogenous base-R1)$_l$-(carbohydrate moiety-R2 and/or R3)$_m$-(phosphate)$_n$-(carbohydrate moiety-R2 and/or R3)$_o$-(nitrogenous base-R4)$_p$ and salts and hydrates thereof, where the nitrogenous base and the carbohydrate moiety are among those found in NADH, NAD, TNAD, PAAD, CoA, FAD, NADP and NADPH, l=0 or 1, m=0, 1, 2, 3 or 4, n=0, 1, 2 or 3, o=0, 1, 2, 3 or 4, p=0 or 1, at least one of m, n and o is at least 1, m+o is not greater than 4, and no more than three of l, m, n, o, and p may be 0, where R1=H, COOH, CONH$_2$, COOCH$_3$, COOC$_2$H$_5$, COOC$_3$H$_7$, CONHCH$_3$, CON(CH$_3$)$_2$, CSNH$_2$, NH$_2$, NHCH$_3$, N(CH$_3$)$_2$, COH, F, Cl, Br, I, OH, OCH$_3$, or OC$_2$H$_5$, R2=H or PO$_3$H, R3=H or PO$_3$H, R4 is H, COOH, CONH$_2$, COOCH$_3$, COOC$_2$H$_5$, COOC$_3$H$_7$, CONHCH$_3$, CON(CH$_3$)$_2$, CSNH$_2$, NH$_2$, NHCH$_3$, N(CH$_3$)$_2$, COH, F, Cl, Br, I, OH, OCH$_3$, or OC$_2$H$_5$, and when n is 0, at least one R2 and/or R3=PO$_3$H; and contacting said antifreeze protein with an amount of said enhancer in an aqueous solution to form a combination, wherein the combination has a thermal hysteresis activity level of at least double said baseline thermal hysteresis.

2. The process of claim 1, wherein the antifreeze protein is recombinant.

3. The process of claim 1, wherein the enhancer comprises the structure:

(nitrogenous base-R1)$_l$-(carbohydrate moiety-R2 and/or R3)$_m$-(phosphate)$_n$-(carbohydrate moiety-R2 and/or R3)$_o$-(nitrogenous base-R4)$_p$ and salts thereof;
where:
l=0 or 1;
m=0 or 1;
n=0, 1, 2 or 3;
o=0 or 1; and
p=0 or 1;

with a proviso that only one of l, m, n, o, and p may be 0;
and where:
the nitrogenous base is pyridinium, hydropyridinyl, purinyl, flavinyl or uridyl;
the carbohydrate moiety is ribose, ribitol, glucosyl or 2-deoxyglucosyl;
R1=H, COOH, CONH$_2$, COOCH$_3$, COOC$_2$H$_5$, COOC$_3$H$_7$, CONHCH$_3$, CON(CH$_3$)$_2$, CSNH$_2$, NH$_2$, NHCH$_3$, N(CH$_3$)$_2$, COH or F;
R2=H or PO$_3$H;
R3=H or PO$_3$H; and
R4 is H, COOH, CONH$_2$, COOCH$_3$, COOC$_2$H$_5$, COOC$_3$H$_7$, CONHCH$_3$, CON(CH$_3$)$_2$, CSNH$_2$, NH$_2$, NHCH$_3$, N(CH$_3$)$_2$, COH or F.

4. A process for protecting a product selected from the group consisting of animal tissues, animal cells, plant tissues, plant cells, and prepared food from damage or injury caused by freezing, comprising the process of claim 1, and adding the combination to the product.

5. The process of claim 4, wherein the product is animal tissue or animal cells.

6. The process of claim 4, wherein the product is plant tissue or plant cells.

7. The process of claim 4, wherein the product is prepared food.

8. The process of claim 7, comprising adding the antifreeze protein and the enhancer to at least one ingredient of the prepared food, and preparing the prepared food with the antifreeze protein and the enhancer in the at least one ingredient.

9. The process of claim 7, wherein the antifreeze protein is a food grade antifreeze protein.

10. The process of claim 1, wherein the enhancer is NADPH, NAPD, NADH, NAD, TNAD, and/or PAAD.

11. The process of claim 1, wherein the enhancer is NADPH and/or NAPD.

12. The process of claim 1, wherein the combination has a thermal hysteresis activity level of at least 4× said baseline thermal hysteresis.

13. The process of claim 12, wherein the combination has a thermal hysteresis activity level of at least 6× said baseline thermal hysteresis.

14. The process of claim 13, wherein the combination has a thermal hysteresis activity level of at least 8× said baseline thermal hysteresis.

15. The process of claim 14, wherein the combination has a thermal hysteresis activity level of at least 10× said baseline thermal hysteresis.

16. The process of claim 1, wherein the antifreeze protein has the partial amino acid sequence of DAFP-1 (SEQ ID NO: 2):

```
QCTGG SDCRS CTVSC TDCQN CPNAR TACTR
      SSNCI NALTC TDSYD CHNAE TCTRS
      TNCYK AKTCT GSTNC YEATA CTDST
      GCP.
```

17. The process of claim 3, wherein m=1 and R2=PO$_3$H, n=1, 2 or 3, and/or o=1 and R3=PO$_3$H.

18. The process of claim 1, wherein said enhancer is present in said combination in a concentration of from 0.08 M to 0.8 M.

19. The process of claim 1, wherein the polypeptides or proteins have an amino acid sequence that differs from the partial amino acid sequence of SEQ ID NO: 2 by one or two amino acids.

20. The process of claim 1, wherein the antifreeze protein has the following amino acid sequence of DAFP-1 (SEQ ID NO: 1):

> MVWVC KSSIL VISVV LMYVC HECYG
>   QCTGG SDCRS CTVSC TDCQN CPNAR
>   TACTR SSNCI NALTC TDSYD CHNAE
>   TCTRS TNCYK AKTCT GSTNC YEATA
>   CTDST GCP.

21. The process of claim 1, wherein the AFP exhibits more than 70% homology with the partial amino acid sequence of SEQ ID NO: 2.

22. The process of claim 1, wherein the AFP exhibits more than 80% homology with the partial amino acid sequence of SEQ ID NO: 2.

23. The process of claim 20, wherein the AFP exhibits more than 70% homology with the above amino acid sequence of SEQ ID NO: 1.

24. The process of claim 20, wherein the AFP exhibits more than 80% homology with the above amino acid sequence of SEQ ID NO: 1.

\* \* \* \* \*